United States Patent
Hart et al.

(10) Patent No.: US 6,921,025 B2
(45) Date of Patent: Jul. 26, 2005

(54) UNIT FOR THE TRANSFER AND DISTRIBUTION OF A LIQUID AND METHOD OF MANUFACTURING THE SAME

(75) Inventors: Gerald Leslie Hart, Surbiton (GB); Guy Edward Naish, Narborough (GB); Kishen Gohil, New Malden (GB)

(73) Assignee: Givaudan SA, Vernier (CH)

( * ) Notice: Subject to any disclaimer, the term of this patent is extended or adjusted under 35 U.S.C. 154(b) by 10 days.

(21) Appl. No.: 10/770,039

(22) Filed: Feb. 2, 2004

(65) Prior Publication Data

US 2004/0164181 A1 Aug. 26, 2004

Related U.S. Application Data

(62) Division of application No. 09/856,744, filed as application No. PCT/EP00/07489 on Aug. 2, 2000, now Pat. No. 6,708,897.

(30) Foreign Application Priority Data

Sep. 29, 1999  (EP) .............................................. 99810876

(51) Int. Cl.⁷ ................................................ A24F 25/00
(52) U.S. Cl. ............................ 239/45; 239/34; 239/43; 239/44
(58) Field of Search ............................... 239/34, 43, 44, 239/45, 145, 326

(56) References Cited

U.S. PATENT DOCUMENTS

| 4,419,326 A | 12/1983 | Santini |
| 4,915,301 A | 4/1990 | Munteanu |
| 5,725,152 A | 3/1998 | Akyu |

FOREIGN PATENT DOCUMENTS

| DE | 41 40 127 C1 | 12/1992 |
| WO | WO 98/16262 | 4/1998 |

*Primary Examiner*—David A. Scherbel
*Assistant Examiner*—Thach H. Bui
(74) *Attorney, Agent, or Firm*—Norris McLaughlin & Marcus PA (57) ABSTRACT

A unit (1) for the transfer and distribution of a liquid (27) using capillary action has an elongated shaft (2) and a screen (3). The shaft (2) includes a first capillary medium (4) suitable for drawing the liquid (27) from a reservoir (26) into the shaft (2) when a bottom portion (20) of the shaft (2) is disposed in the liquid. The screen (3) is connected to the shaft (2) and includes a second capillary medium (5) suitable for receiving the liquid (27) drawn by the first capillary medium (4) and distributing it over at least a major part of the screen (3) where it evaporates.

21 Claims, 11 Drawing Sheets

UNIT FOR THE TRANSFER AND DISTRIBUTION OF A LIQUID AND METHOD OF MANUFACTURING THE SAME

This application is a division of application Ser. No. 09/856,744, filed May 25, 2001, now U.S. Pat. No. 6,708,897, which is a 371 of PCT/EP00/07489, filed Aug. 2, 2000.

The present invention relates to a unit for the transfer and distribution of a liquid and a method of manufacturing the same according to claims 1 respectively 12. The invention further relates to a refill for a dispenser for volatile liquids according to claim 16.

BACKGROUND OF THE INVENTION

In order to transfer liquids it is known to use capillary action which is dependent on the cohesive forces within the liquid and the adhesive forces of the liquid to a capillary medium comprising small channels, e.g. pores or spaces between fibers. Such a capillary medium, e.g. a wick, being introduced through an opening into a reservoir, can therefore be used to draw a liquid out of said reservoir passively by means of capillary action only, i.e. without additional sucking. The transferred liquid may be used to distribute chemical substances to the ambient air in order to generate or mask an odour, to evoke a medical or organoleptic effect or to affect insects.

The U.S. Pat. No. 5,114,625 discloses a fragrance dispenser with a liquid reservoir and a wick with a liquid receiving end disposed in the reservoir for drawing liquid therefrom into the wick. A portion of the wick length is exposed to an air flow provided by a fan.

However, the distribution of volatile chemical substances contained in the liquid in the air flow is not sufficiently homogenous when the air flow is brushing over the wick. Further, in most cases dispensing a substance cannot be done without generation of an external air flow in order to evaporate a given amount of liquid per unit time.

The wicks used in prior art dispensing devices are difficult to exchange as they have to be mounted in such a way that the wick is arranged in a defined position relative to the reservoir. This is rendered difficult as wicks are generally soft. Further, the reservoir including the wick has to be tight to prevent spilling of the liquid and uncontrolled evaporation. The same problem arises with a refill for such a device. A refill already including a wick has to be tightly sealed before use, while refill and wick separated from each other have to be such that the wick is easy and clean to insert and the refill is tight before and during use.

It is therefore an object of the invention to provide a unit for the transfer and distribution of a volatile liquid that has a good efficiency in evaporating liquid, is easy and cheap to manufacture and is easily and hygienically insertable into a reservoir, especially the reservoir of a refill.

It is another object of the invention to provide a method of manufacturing such an improved transfer unit.

It is a further object of the invention to provide a refill suited for the use with such a transfer unit.

SUMMARY OF THE INVENTION

The above and other objects of the invention are achieved by a transfer unit as specified in claim 1, a method of manufacturing the same as specified in claim 12, a refill as specified in claim 16 and a dispenser with such a transfer unit and such a refill.

According to the invention a shaft comprising a first capillary medium to draw a liquid into the shaft due to capillary action, e.g. a wick, scrib rod or a porous rod, is provided with an integrated screen to serve as an enlarged liquid receiving area from which the liquid is easily evaporated to the ambient air. To provide an enlarged area, the screen is preferably at least two to three times as wide as the shaft. By capillary action the liquid is drawn from the shaft to the screen and distributed over it, using a second capillary medium connected to the first capillary medium. As first capillary medium in general any material capable of absorbing and transferring a liquid due to capillary action is suited, e.g. material containing natural or synthetic fibers, woven or non-woven fabrics, porous media, capillary tubes, or a rod with external grooves, e.g. as described in U.S. Pat. No. 4,913,350. As second capillary medium a material with open pores from which liquid evaporates is suited, e.g. material containing natural or synthetic fibers, woven or non-woven fabrics, porous media. In a preferred embodiment first and second capillary medium are a single piece, for example shaft and screen are made of a sheet of card board or non-woven welded or laminated material, which is cheap and therefore suited for the production of a mass article. Shaft and screen are preferably rigid to maintain the shape of the transfer unit and its position with respect to the reservoir when introduced into the dispenser.

In a preferred embodiment of the invention the screen is permeable to air flow through the screen in a direction approximately normal to the plane of the screen. This can be achieved by a screen having one or more openings. In one preferred embodiment there are a plurality of "small" openings, each with an area less than 5% of the total screen area, distributed preferably uniformly over the screen and result in openings in the screen totalling no more than 95%. By the screen material itself being capillary at least between the openings the liquid is distributed over the screen and around the openings where it evaporates. Additionally or alternatively, the openings or the whole screen area can be covered with another air permeable capillary medium, such as a gauze sheet or tissue paper, which additionally respectively solely receives and distributes the liquid. In this case there is not need for the openings being "small", i.e. one or more "bigger" openings each with an area of equal to or greater than 5% of the total screen area can be used to transmit the air. To enhance evaporation, an externally generated air flow is advantageous but not essential.

The refill according to the invention comprises a reservoir containing the liquid, an outlet opening and a shaft receiving passage starting at the outlet opening and projecting inward. The shaft receiving passage is suitable for receiving the shaft of the transfer unit as described above. Preferably the receiving passage is dimensioned to tightly embrace the shaft, as this stabilizes the transfer unit and a capillary effect can be achieved between the shaft and the walls of the receiving passage enhancing the capillary action of the shaft itself. Another embodiment of the shaft may be envisaged where lower-capillary action is required. This can be achieved through tapering of the shaft for the lower portion of ist length, such that it is not in intimate contact wiht the lower portion of the receiving passage. The refill and the shaft receiving passage may be moulded in one piece which can be produced at low cost. In a preferred embodiment the shaft receiving passage comprises a seal, e.g. a metal foil, plastic moulding, or any inpervious material that can be easily punctured isolating the liquid in the reservoir from the outside. Preferably, the seal is located at the bottom end of the passage and may be punctured by the shaft when fully introduced into the refill. A commercial embodiment of this could have the shaft partially introduced into the shaft receiving passage and the action of inserting the refill into the main unit causes the shaft to break the seal. To facilitate breaking the seal the shaft preferably comprises a cutting member at its bottom portion, e.g. a tip or a thorn or a knife-like element. Seal location at the bottom end of the passage is advantageous as the narrow passage protects the seal against accidental damage. The refill can thus be sold ready for use without an extra cover of the outlet opening, such as a lid, thus saving material, waste and manufacturing costs. Introduction of the shaft can be accomplished without spilling.

The transfer unit is preferably sold in a blister package containing one or more transfer units or a refill and an isolated unit insertable into the refill.

A coating of the lateral shaft faces respectively a layer around these faces impermeable to liquid is advantageous as it prevents softening of the shaft and stabilizes the shaft. Further, it enables the control of the dispensed amount as liquid flow can be stopped by tilting or turning the reservoir, thus preventing contact of the bottom portion with the liquid.

BRIEF DESCRIPTION OF THE DRAWINGS

FIG. 8b shows a method of manufacturing transfer units as shown in FIG. 2 using the sheet of FIG. 8a;

DETAILED DESCRIPTION OF THE PREFERRED EMBODIMENTS

Figure 1:
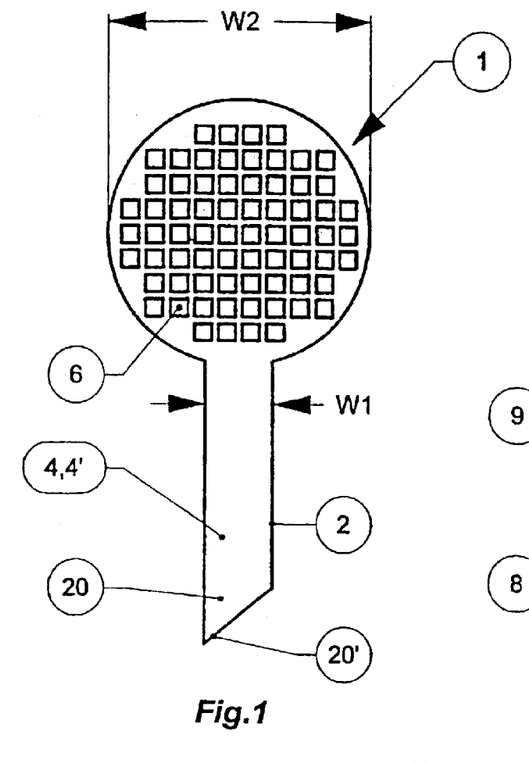
FIG. 1 shows a transfer unit with a shaft and a screen with a plurality of "small" openings.
Figure 5A:
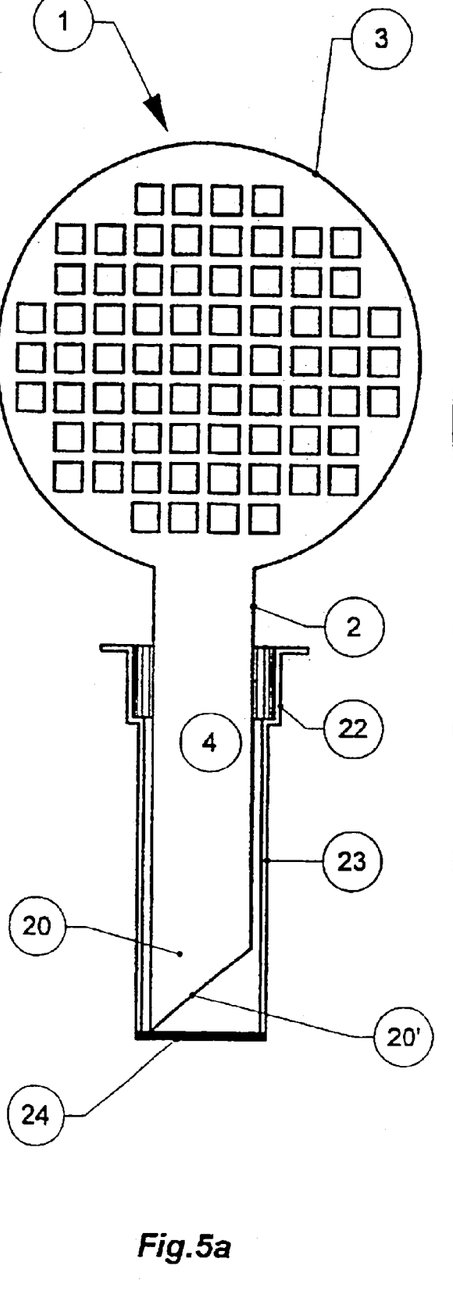
FIG. 5a,b shows the insertion of a transfer unit into the shaft receiving passage of FIG. 4a-c.
Figure 5B:
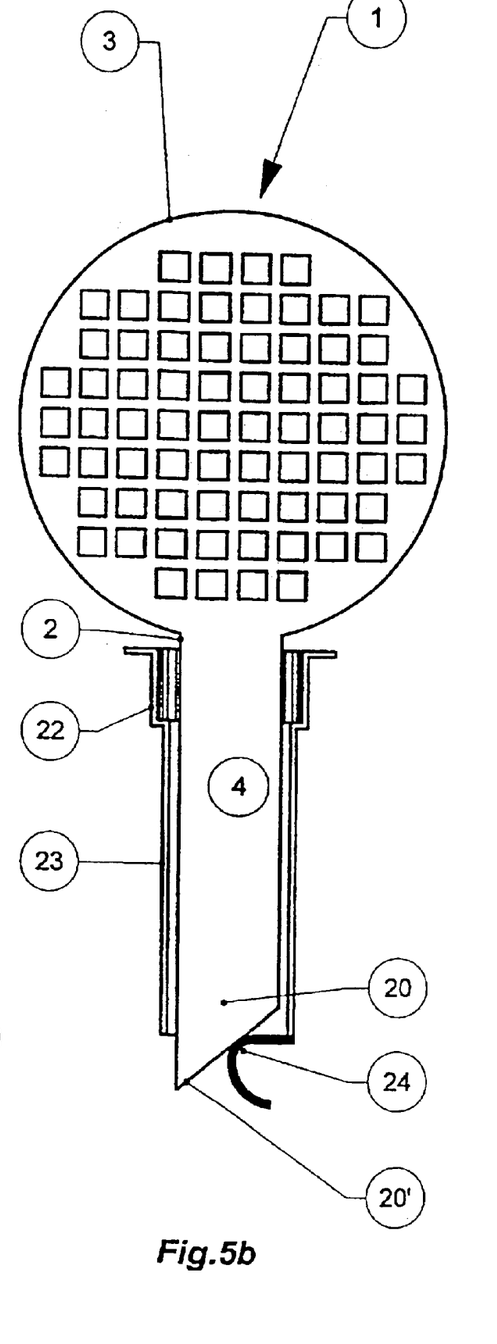

FIG. 1 shows a transfer unit 1 with an elongated shaft 2 and a screen 3. The shaft 2 consists of a first capillary medium 4, here absorbent card board 4', preferably 1 to 4 mm thick. The shaft 2 may have, but is not restricted to a rectangular shape with a width W1 of preferably 5 to 10 mm. The length of the shaft 2 is greater than the width W1 and is chosen such that at least the bottom portion 20 of the shaft 2 is in contact with the liquid, e.g. a perfume, when introduced into a liquid reservoir. The bottom portion 20 has a tip 20' to facilitate breaking a seal, as shown in FIG. 5a,b. The screen 3 consists of a second capillary medium 5 with a plurality of "small" openings 6 punched out to allow air to pass through, each opening 6 covering less than 5% of the total screen area. The width W2 of the circular screen 3 is about three times the width W1 of the shaft 2. Screen 3 and shaft 2 are made of the same material, a card sheet, i. e. in this embodiment for the second capillary medium 5 the same material as for the first capillary medium 4 is used. Alternatively, different capillary materials could be connected to enable liquid transfer to the screen 3.

Figure 2:
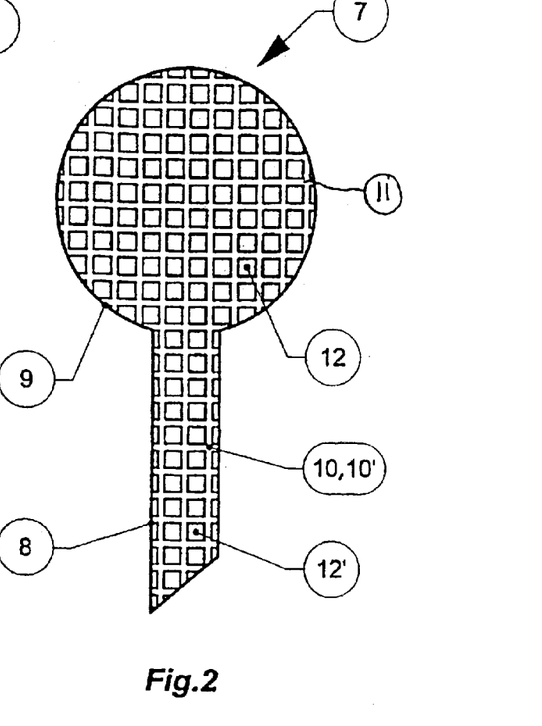
FIG. 2 shows a transfer unit with a shaft and a screen both having a plurality of "small" openings.
Figure 8A:
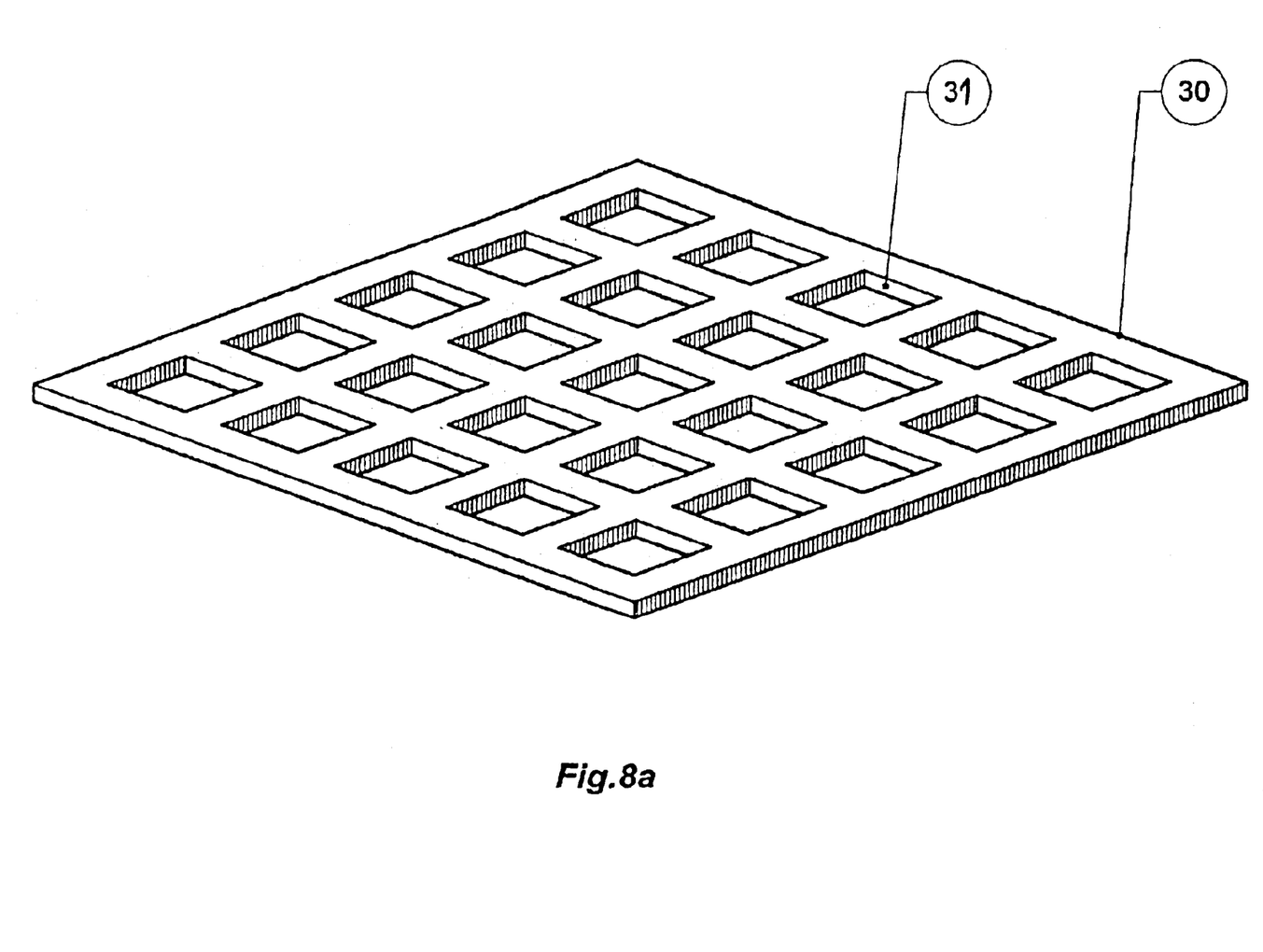
FIG. 8a shows an example of a perforated sheet as a sheet material for transfer units as shown in FIG. 2.

FIG. 2 shows another example for a transfer unit 7 with a shaft 8 and a screen 9 both having a plurality of "small" openings 12, 12'. Its shape is generally the same as of the unit of FIG. 1. As a capillary material for the capillary media 11 and 10 of screen 9 respectively shaft 8 an absorbent card 10' with perforations that constitute the openings 12, 12' is used, e.g. as shown in FIG. 8a.

Figure 3:
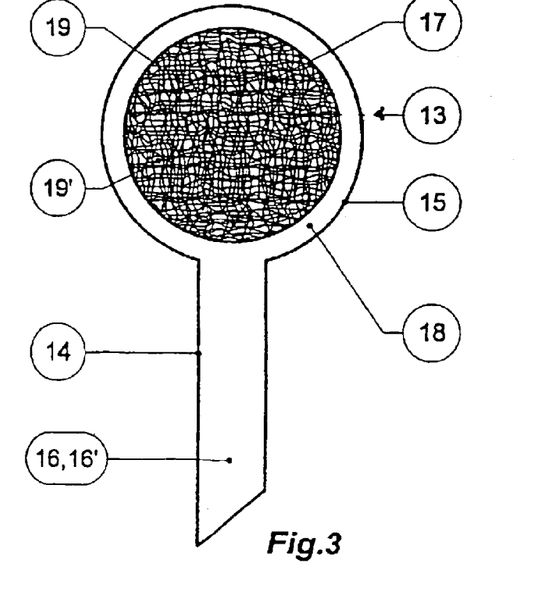
FIG. 3 shows a transfer unit with a shaft and a screen having one "big" opening.
Figure 3A:
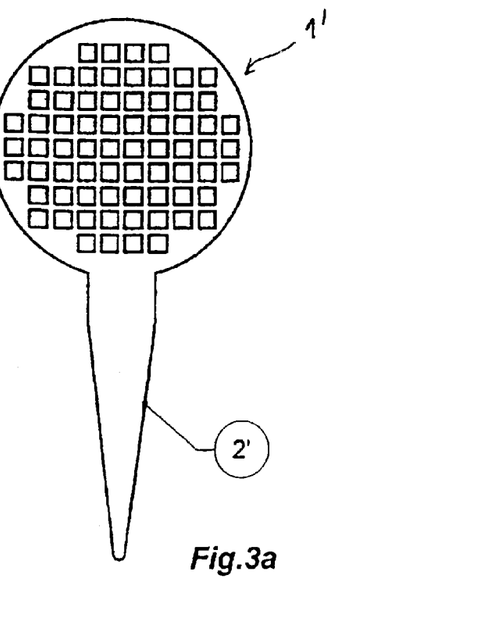
FIG. 3A shows a generic shaft which may have screens as depicted in FIG. 1-3, but has tapered lower portion.

FIG. 3 shows a third example for a transfer unit 13 with a shaft 14 and a screen 15. The screen 15 comprises an annular frame 18 with a central opening 17, that covers approximately 80% of the screen area ("big" opening). The opening 17 is covered with a sheet of capillary air permeable material, here a gauze sheet 19'. The gauze sheet 19' receives as a second capillary medium 19 liquid drawn into the shaft 14 and to the screen 15 by the first capillary medium 16. The frame 18 is made of the same material as the shaft 14, here card board 16, i.e. the frame contributes to the distribution and transfer of the liquid to the gauze sheet 19' using capillary action. FIG. 3A shows a transfer unit 1' with an elongated shaft 2' and a screen 3. The shaft 2' consists of a first capillary medium 4' preferably 1 to 4 mm thick. The shaft 2' has a rectangular shape at its upper most portion directly below the screen, and a triangular taper for the remainder of its length with the taper comprising of 5% to 95% of the total length of the shaft. The length of shaft 2' is greater than the maximum width and is chosen such that at least the bottom portion of the shaft is in contact with the liquid.

In another embodiment (not shown) the frame 18 is made of a non capillary material, such as plastic or metal, serving to stabilise the second capillary medium 19 which is connected to the shaft for liquid transfer. In yet another embodiment (not shown) the shaft itself comprises a frame made of non capillary material stabilising a first capillary medium, e.g. a gauze sheet or a tissue paper, being connected to the second capillary medium, preferably the second capillary medium being an integral part of the first capillary medium.

Figure 4A:
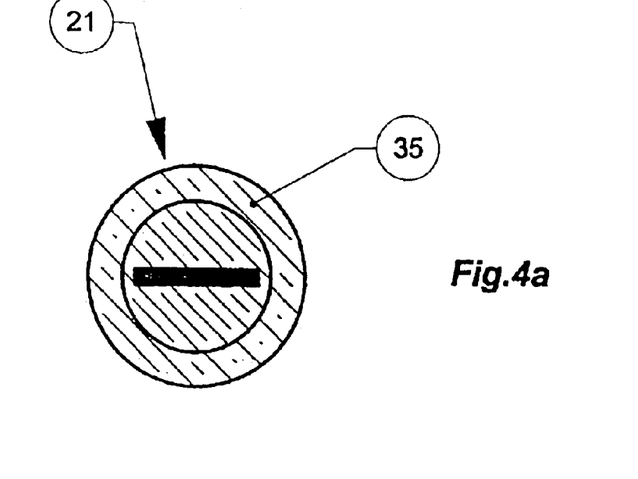
FIG. 4a-c shows different views of a shaft receiving passage.
Figure 4B:
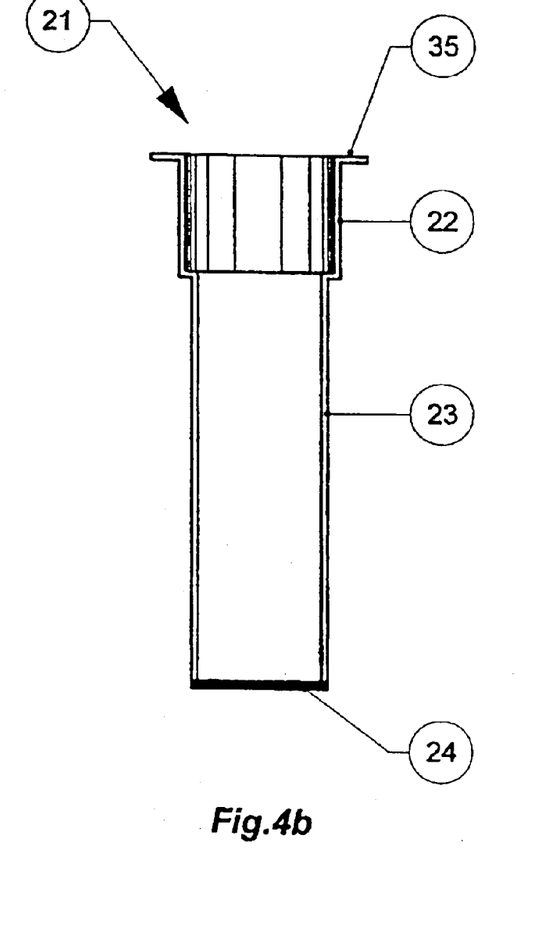
Figure 4C:
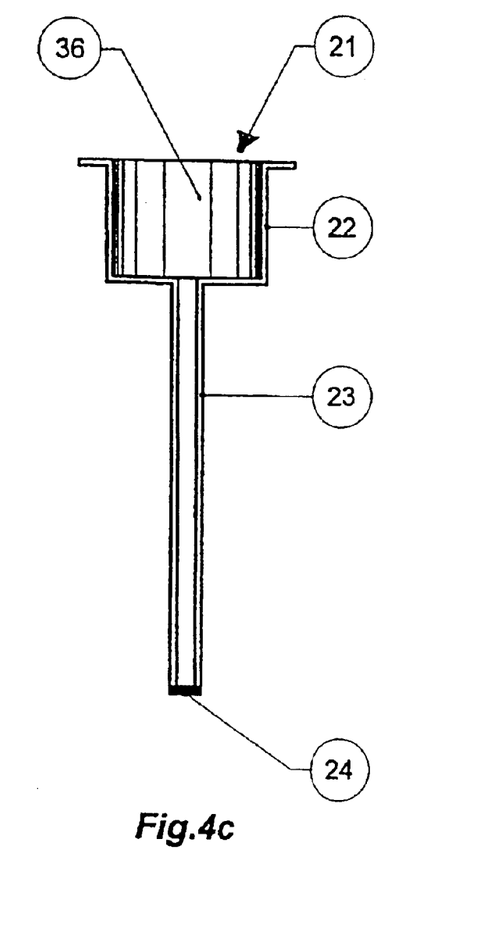
Figure 6A:
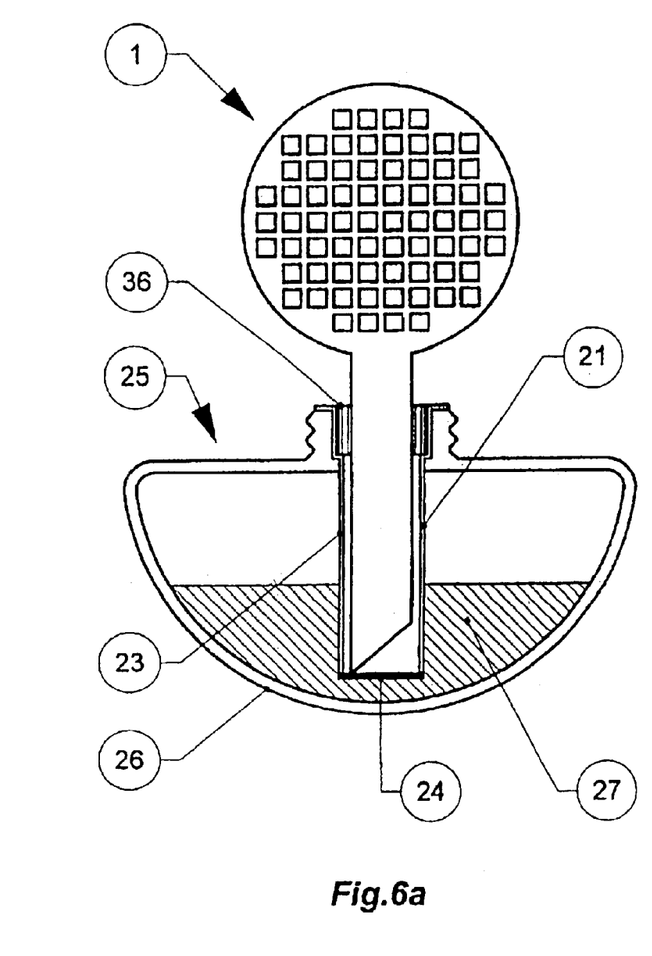

FIG. 4a-c shows different views of a shaft receiving passage 21 dimensioned to receive the shaft of a transfer unit. A transfer unit 1 being introduced into the receiving passage 21 is shown in FIG. 5a,b. The receiving passage 21 may be an integral part of a refill for an air freshener or the like, as shown in FIG. 6a, b, or may be suited for insertion into the outlet opening of a liquid reservoir.

The receiving passage 21 comprises an elongated sleeve 23 having a rectangular cross section dimensioned to tightly embrace the shaft 4 of transfer unit 1. The receiving passage 21 further comprises a fitting 22 adjacent to the sleeve 23 having circular cross section. The fitting is dimensioned to tightly fit into a circular outlet opening of a liquid reservoir 26. The fitting 22 comprises an annular flange 35 to seal the outlet opening when the passage 21 is inserted. In case the receiving passage is an integral part of the liquid reservoir 26 the fitting 22 is not essential as the passage 21 and the reservoir 26 can be moulded in one piece. The passage 21 guides the transfer unit 1 into a defined position with respect to the dispensing device, e.g. to a fan generating an air flow. In this position transfer unit 1 is mechanically stabilised by passage 21.

Figure 5C:
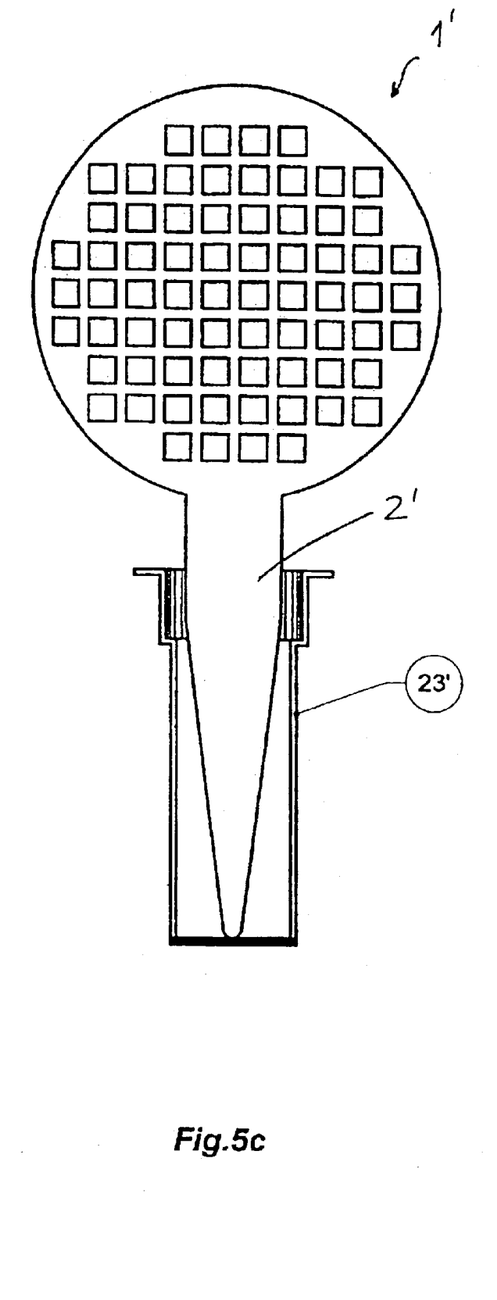
FIG. 5c,d shows a view of a shaft receiving passage with the tapered shaft as shown on FIG. 3A FIG. 6a,b shows a refill with a transfer unit.
Figure 5D:
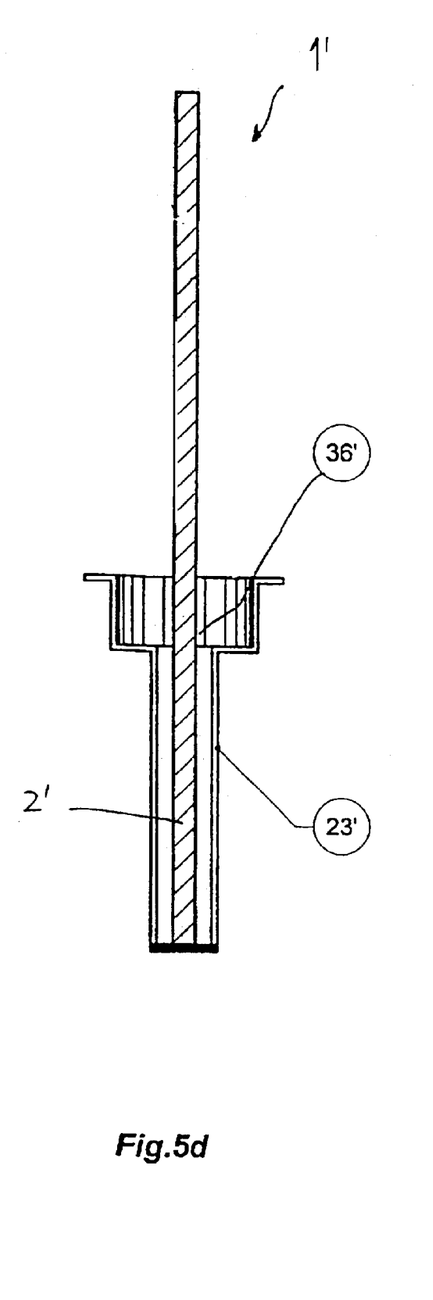

FIG. 5c-d are similar to FIG. 4b-c except that they depict a shaft receiving passage 23' containing a tapered shaft 2', as shown in FIG. 3a. The receiving passage has a cross section dimensioned as not to tightly embrace the shaft 2' hence leaving a gap between the shaft and receiving passage of at least 1 mm on both front and back sides. In this embodiment there will be a tight; fitting portion at the top 36' of the receiving passage 23' to hold the transfer unit 9' in place.

Figure 6B:
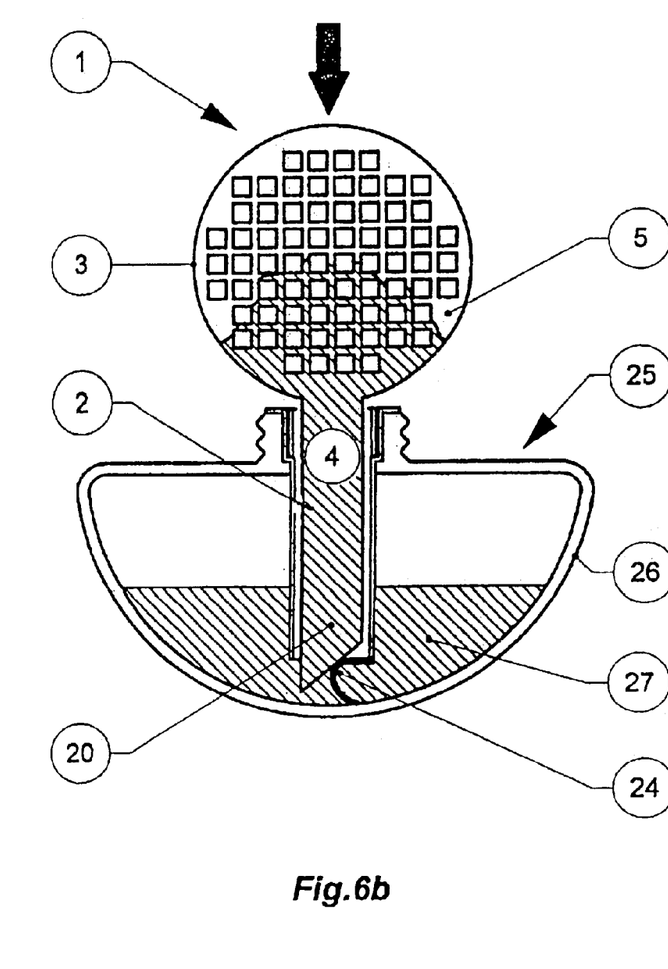

The bottom opening of the passage 21 is closed with a foil seal 24 that can be punctured by the shaft 4 as shown in FIGS. 5b and 6b. The seal 24 isolates the liquid 27 contained in the reservoir 26 of the refill 25 from the outside, no extra lid is needed. When the transfer unit 1 is inserted, the tip 20' of its bottom portion 20 breaks the seal 24, the liquid 27 has access to the shaft 4 immediately, is drawn up to the screen 3 and evaporated.

FIGS. 7, 8b and 9a–c show methods of manufacturing the transfer units as shown in FIG. 1 to 3. The transfer unit of FIG. 1 is manufactured by punching a shape 29 with a circular main body 29', forming the screen afterwards, and an elongated part 29", forming the shaft, from a sheet 28 of capillary material. This shape 29 can be punched in one go with a plurality of holes 29''' arranged within the main body shape 29' or before or after punching the holes 29'''.

A pre-perforated sheet or mat 30 of capillary material with a plurality of holes 31 as shown in FIG. 8a serves as basis for manufacturing transfer units shown in FIG. 2. A shape 29 as, described above is punched from the sheet 30. The cut out shape is ready to use as a transfer unit.

Figure 9A:
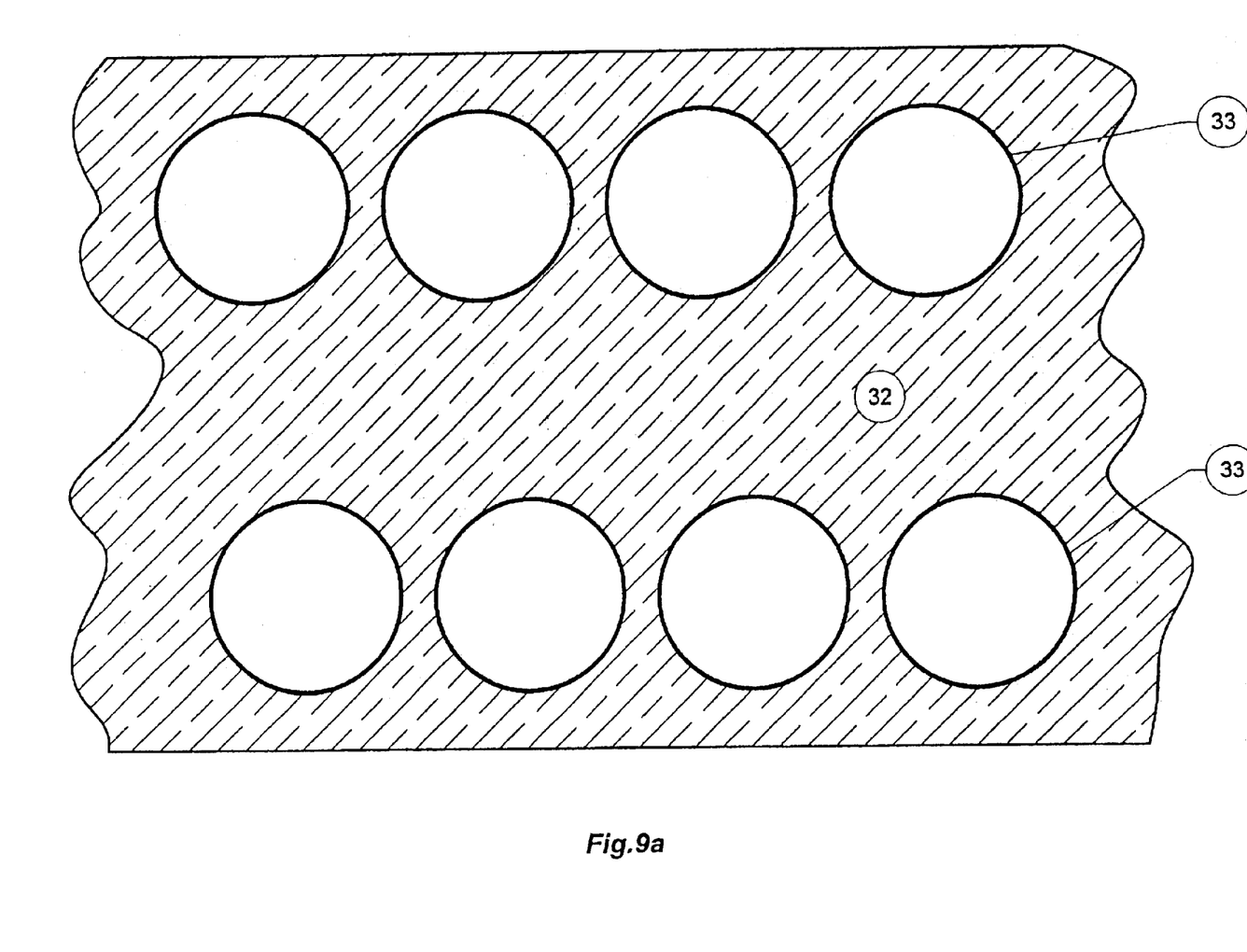
FIG. 9a,b shows a method of manufacturing transfer units as shown in FIG. 3.
Figure 9B:
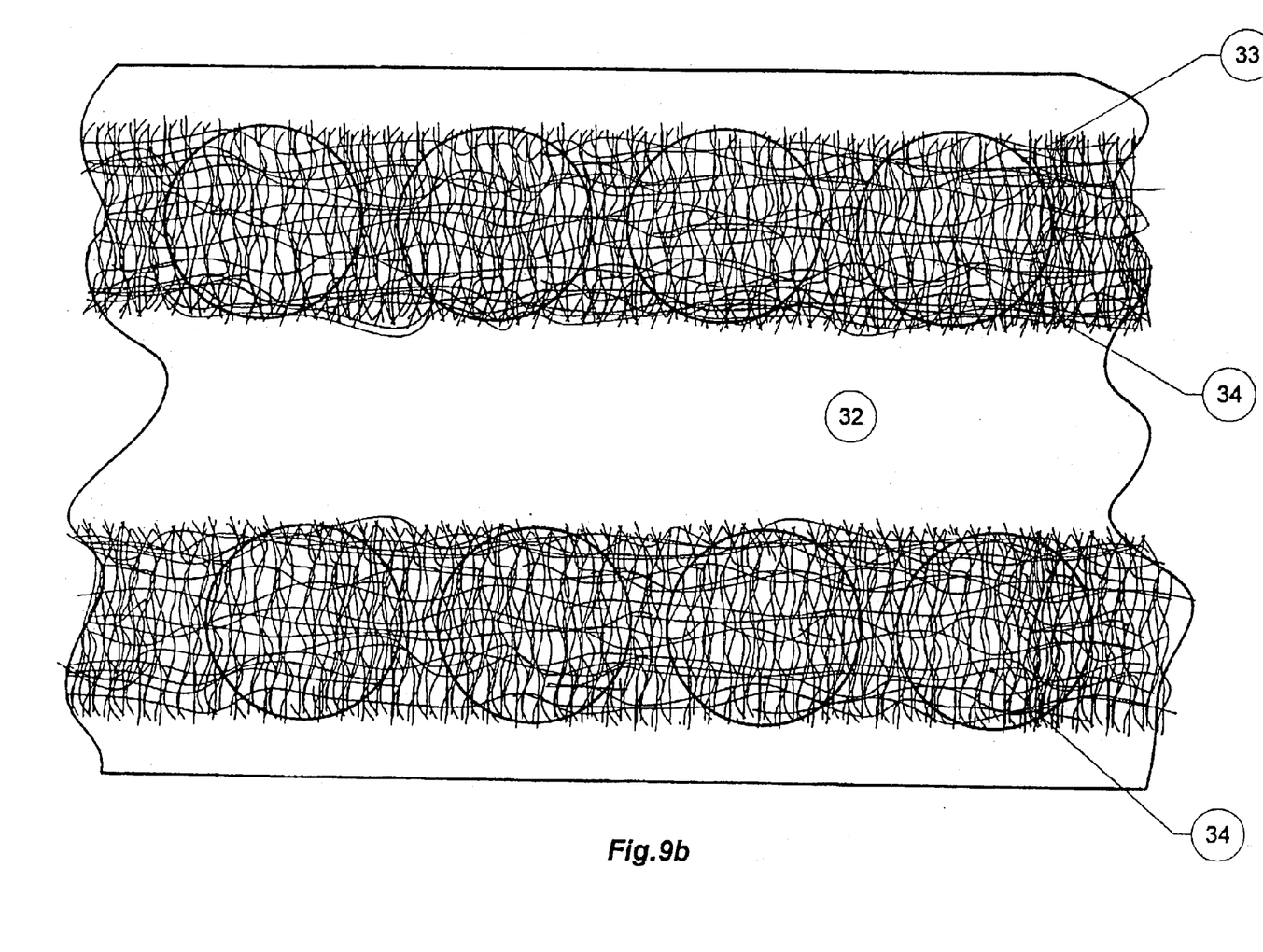
Figure 9C:
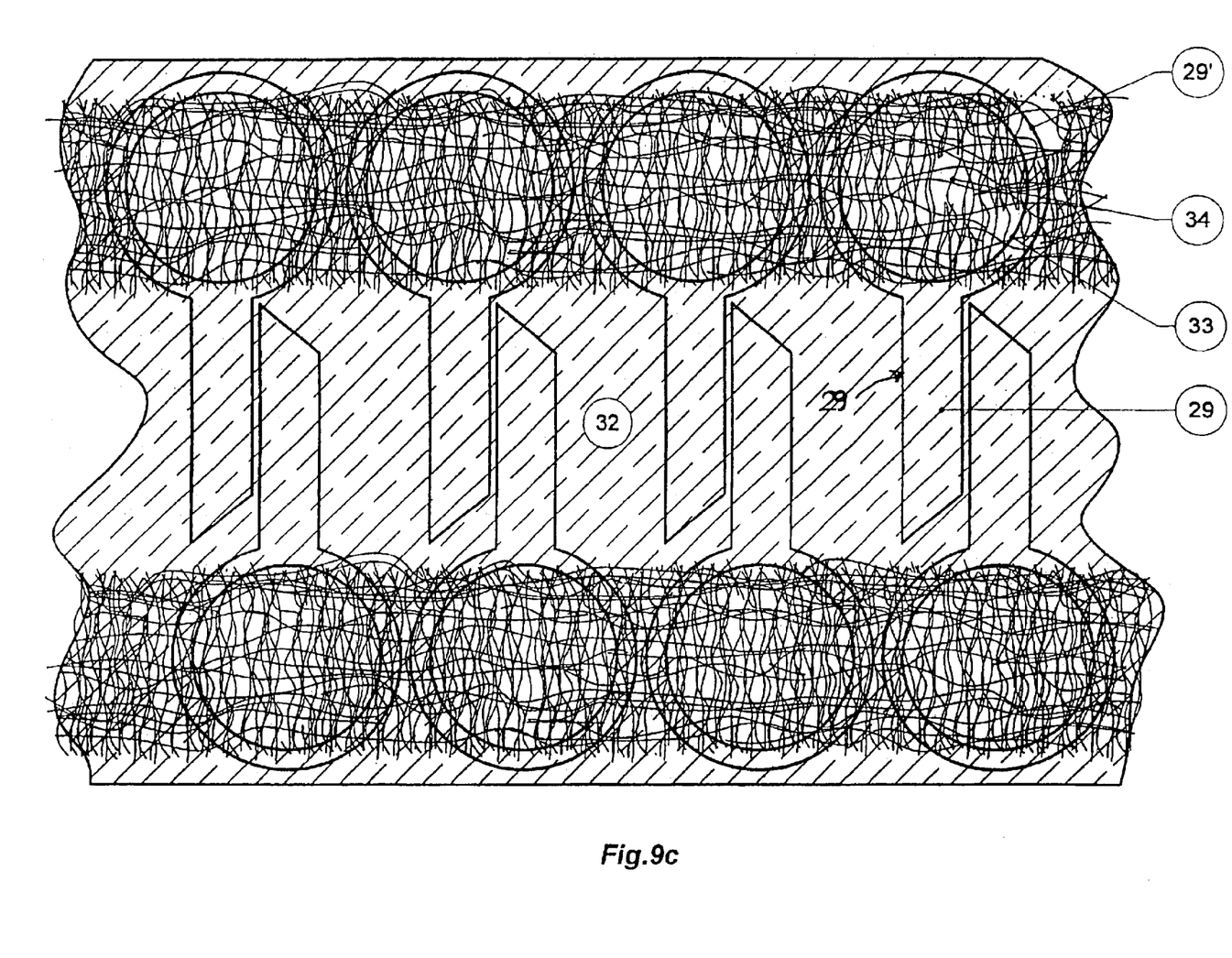

The steps of an alternative manufacturing method are depicted in FIG. 9a-c, where "big" holes 33 are punched from a continual mat or sheet 32 (FIG. 9a). Then a strip of continual air permeable capillary material 34 such as gauze is glued over the holes 33 (FIG. 9b). A shape 29 as described above is punched from the sheet 32, where the shape 29 is positioned such that each hole 33 is located in the center of the circular main body 29'.

Figure 7:
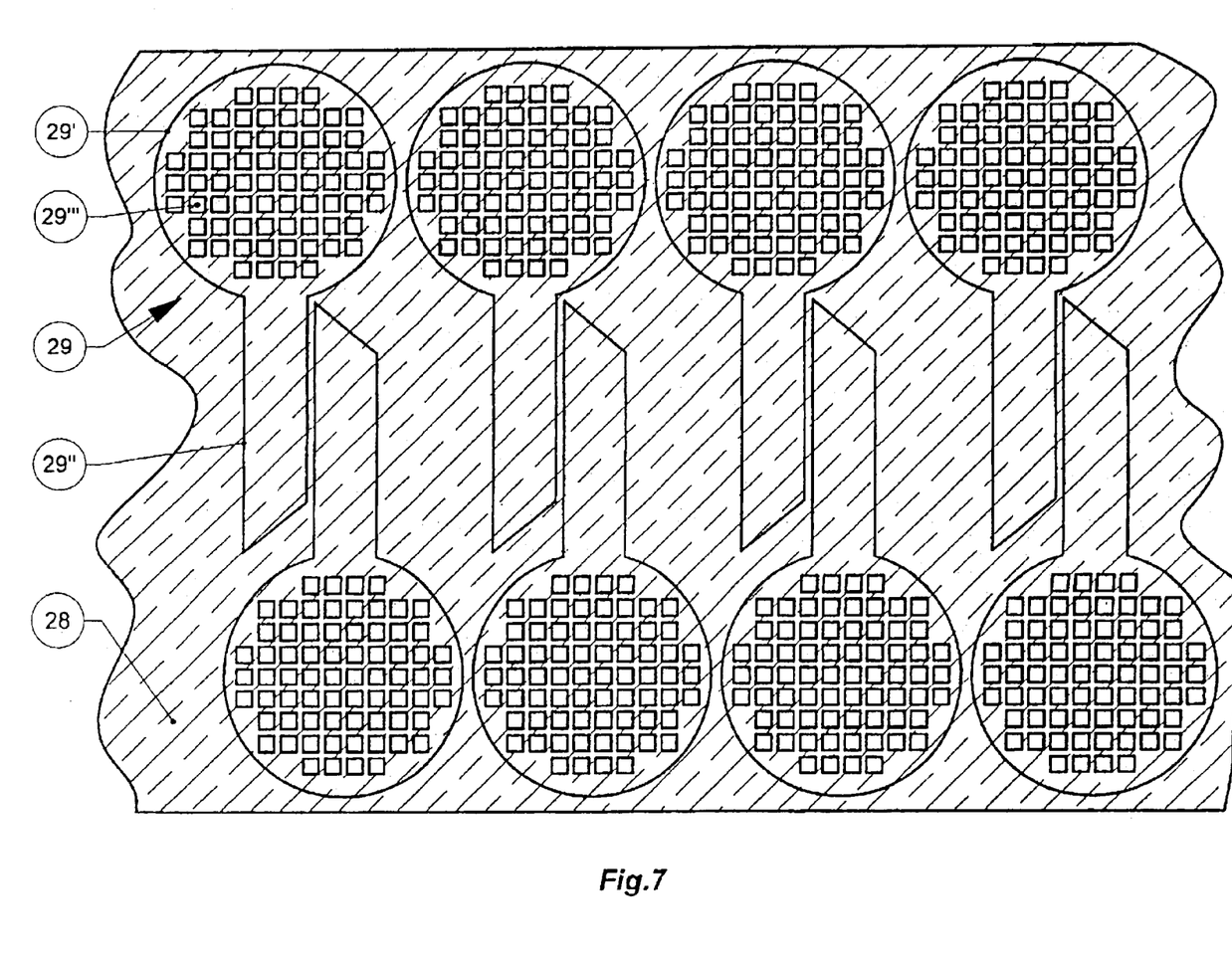
FIG. 7 shows one method of manufacturing the transfer units as shown in FIG. 1.
Figure 8B:
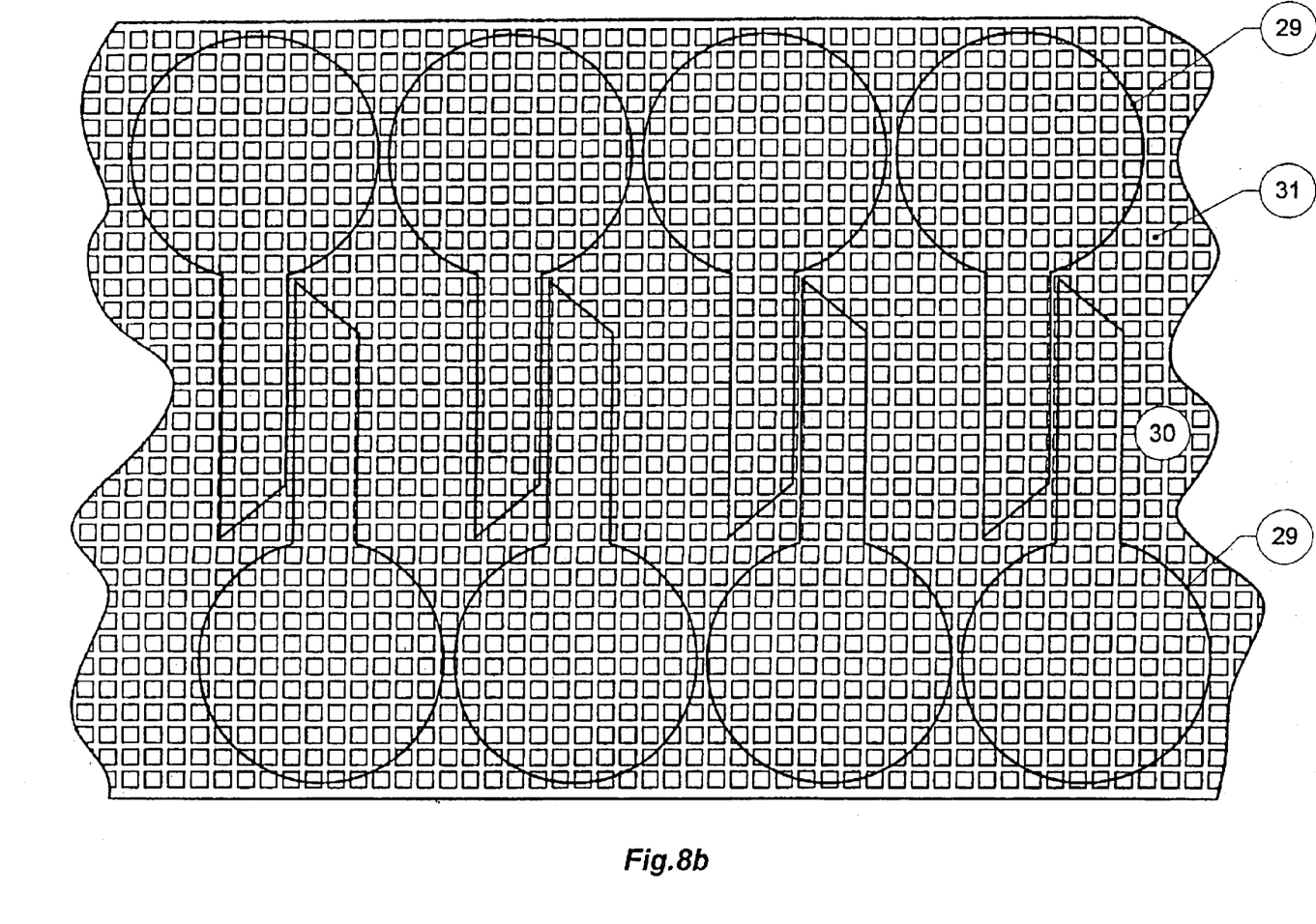

The inventive transfer units 1, 7, 13 as shown above can thus be manufactured at very low cost as the materials used, e.g. gauze, cardboard, fleece, are cheap and the methods of manufacturing described in FIG. 7 to 9 involve three steps at most.

What is claimed is:

1. A transfer unit (1, 1', 7, 13) for the transfer and distribution of a liquid (27) using capillary action with an elongated shaft (2, 2', 8, 14) including a first capillary medium (4, 10, 16),
    suitable for drawing the liquid (27) from a reservoir (26) and with a screen (3, 9, 15) including a second capillary medium (5, 11, 19) suitable for receiving the liquid (27) from the first capillary medium (4, 10, 16) and distributing it over at least a part of the screen (3, 9, 15) for evaporation
    and wherein the screen (3, 9, 15) is at least partially made of a capillary material, or a non-woven fleece material, and has one or more openings (6, 12, 17) through which air can be blown, and
    wherein the first capillary medium and the second capillary medium are a single piece.

2. Transfer unit (1, 1', 7, 13) according to claim 1, wherein the screen (3, 9, 15) is permeable to an airflow in a direction approximately normal to the plane of the screen (3, 9, 15).

3. Transfer unit (1, 1', 7, 13) according to claim 1, wherein the screen (3, 9, 15) comprises a planar frame (18) with at least one opening (6, 12, 17), with the second capillary medium (5, 11, 19) being attached to the frame (18) covering the at least one opening (6, 12, 17).

4. Transfer unit (1, 1', 7, 13) according to claim 3, wherein the second capillary medium (5, 11, 19) comprises a sheet (19', 34) of air permeable material, selected from the group consisting of a thin woven fabric, a non-woven fabric, gauze and tissue paper.

5. Transfer unit (1, 1', 7, 13) according to claim 1, wherein the screen is at least partially made of capillary material selected from the group consisting of a cellulose structure and cardboard (4', 10', 16').

6. Transfer unit (1, 1', 7, 13) according to claim 1, wherein the shaft (2, 2', 8, 14) is at least partially made of a capillary material, preferably a cellulose structure such as card (4', 10', 16') or a non-woven fleece material.

7. Transfer unit (1, 1', 7, 13) according to claim 1, wherein the surface of the elongated shaft (2, 2', 8, 14) is permeable to liquid (27) at a bottom portion (20) and impermeable at other portions of the elongated shaft (2, 2', 8, 14).

8. Transfer unit (1, 1', 7, 13) according to claim 7, wherein the elongated shaft (2, 2', 8, 14) further comprises a layer covering the lateral surfaces of the elongated shaft (2, 2', 8, 14), which is impermeable to liquid.

9. Transfer unit (1, 1', 7, 13) according to claim 1, wherein the screen (3, 9, 15) has a width (W2) which is at least twice the shaft width (W1) of the enlongated shaft (2, 2', 8, 14).

10. Transfer unit (1, 1', 7, 13) according to claim 1, wherein the screen (3, 9, 15) and the elongated shaft (2, 2', 8, 14) are a single piece.

11. Transfer unit (1, 1', 7, 13) according to claim 1, wherein the bottom part (20) which includes cutting means (20') to facilitate breaking or cutting a seal (24) in a shaft receiving passage (21) or a refill unit (25) for fragrance dispensers.

12. Method of manufacturing a transfer unit (1, 1', 7, 13) according to claim 1, comprising the step of:
    cutting from a sheet material (28, 30, 32) at least one shape (29, 29', 29") or a transfer unit having an elongated shaft (2, 2', 8, 14) with an attached screen (3, 9, 15), said screen (3, 9, 15) being wider than the elongated shaft (2, 2', 8, 14).

13. Method according to claim 12, wherein the sheet material (28, 30, 32) comprises of a capillary material selected from the group consisting of cardboard, a rigid fleece material, a gauze sheet and tissue paper attached to and covering the sheet material (28, 30, 32).

14. Method according to claim 12, further comprising the step of:
    cutting out at least one opening in at least in those areas of the sheet: material (28, 30, 32) where the screen shape (29') is located.

15. Method according to claim 14, further comprising the step of:
    attaching at least one sheet of air permeable capillary material (34) to the sheet material (28, 30, 32) after cutting the at least one opening (33).

16. Refill (25) for a dispenser for volatile liquids (27) comprising a reservoir (26) containing the liquid (27), an outlet opening (36) and a shaft receiving passage (21) extending from the outlet opening (36) inward suitable for receiving the elongated shaft (2, 2', 8, 14) of the transfer unit of claim 1.

17. Refill (25) according to claim 16, wherein, when the enlongated shaft (2, 2', 8, 14) is introduced into the shaft receiving passage (21), the bottom portion of the elongated shaft (2, 2', 8, 14) is in contact with the liquid (27) and the screen (3, 9, 15) extends above the refill (25) and is exposable to an air flow.

18. Refill (25) according to claim 17, wherein the shaft receiving passage (21) comprises a sleeve (23) dimensioned to receive an elongated shaft (2, 2', 8, 14) and made of a material impermeable to the liquid (27).

19. Refill (25) according to claim 18, wherein the sleeve (23) is dimensioned to tightly embrace the elongated shaft (2, 2', 8, 14) down to or close to its bottom portion (20).

20. Refill (25) according to claim 19, wherein the shaft receiving passage (21) comprises a seal (24) isolating the liquid (27) in the reservoir (26) from the outlet opening.

21. A dispenser comprising a refill (25) comprised of:

(1) a refill (25) for a dispenser for volatile liquids (27) comprising a reservoir (26) containing the liquid (27), an outlet opening (36) and a shaft receiving passage (21) extending from the outlet opening (36) inward suitable for receiving the elongated shaft (2, 2', 8, 14) of the transfer unit of claim 1; and (2) the transfer unit of claim 1.

\* \* \* \* \*